United States Patent [19]

Tanabe et al.

[11] 4,285,872

[45] Aug. 25, 1981

[54] METHOD FOR PRODUCING GLYCIDYL (METHA)ACRYLATE

[75] Inventors: Rippei Tanabe, Nishinomiya; Yuji Yokoyama, Kobe; Jiro Hirano, Takatsuki, all of Japan

[73] Assignee: Nippon Oil and Fats Company, Ltd., Tokyo, Japan

[21] Appl. No.: 62,621

[22] Filed: Aug. 1, 1979

Related U.S. Application Data

[63] Continuation of Ser. No. 910,529, May 30, 1979, abandoned.

[30] Foreign Application Priority Data

Jun. 6, 1977 [JP] Japan .................................. 52/65849

[51] Int. Cl.³ ............................................. C07D 301/00
[52] U.S. Cl. .................................................. 260/348.12
[58] Field of Search .................................... 260/348.12

[56] References Cited

U.S. PATENT DOCUMENTS

| | | | |
|---|---|---|---|
| 2,879,281 | 3/1959 | Brokaw | 260/410.7 |
| 3,836,576 | 9/1974 | Falize et al. | 560/217 |
| 4,002,648 | 1/1977 | Puskas et al. | 260/346.3 |
| 4,074,062 | 2/1978 | Murakami et al. | 560/217 |

FOREIGN PATENT DOCUMENTS

| | | |
|---|---|---|
| 2423405 | 11/1975 | Fed. Rep. of Germany . |
| 2088971 | 1/1972 | France . |
| 52-25713 | 2/1977 | Japan . |
| 753880 | 8/1956 | United Kingdom . |

*Primary Examiner*—Norma S. Milestone
*Attorney, Agent, or Firm*—Stevens, Davis, Miller & Mosher

[57] ABSTRACT

Glycidyl methacrylate or glycidyl acrylate is produced by reacting methyl methacrylate or methyl acrylate with glycide in the presence of a metal salt of a fatty acid.

6 Claims, No Drawings

METHOD FOR PRODUCING GLYCIDYL (METHA)ACRYLATE

This is a continuation of application Ser. No. 910,529 filed May 30, 1979 now abandoned.

The present invention relates to a method for producing glycidyl methacrylate or glycidyl acrylate (referred to as glycidyl (metha)acrylate hereinafter) in an ester interchange reaction of methyl acrylate or methyl methacrylate (referred to as methyl (metha)acrylate hereinafter) and glycide by using a particularly defined catalyst.

It has been already known that glycidyl (metha)acrylate is produced by an ester interchange reaction of methyl (metha)acrylate and glycide in the presence of a catalyst.

For example, (1) a process using phosphines (Japanese Patent Application Publication No. 38,421/72), (2) a process using an alkali alcoholate (Japanese Patent Laid Open Application No. 154,205/75) and (3) a process using an alkali cyanide (Japanese Patent Laid Open Application No. 146,419/76) have been known.

However, when these catalysts are used, there are the following drawbacks, (1) the industrial yield is low, (2) it is difficult to completely prevent the formation of polymer during the reaction and (3) the lowering of the purity of the product due to the side reaction cannot be avoided.

The particularly important drawback is that it is very difficult to completely remove the catalyst from the reaction system when these catalysts are used and therefore it is difficult to obtain glycidyl (metha)acrylate by continuously distilling the reaction mixture. Furthermore, any of the conventional catalysts are dangerous chemicals, so that there are some problems in view of handling in a commercial scale and storage.

The inventors have earnestly investigated in order to overcome these drawbacks and as the result, it has been found that a metal salt of a fatty acid is very effective and commercially advantageous as the catalyst for the above described ester interchange reaction and the present invention has been attained.

Metal salts of fatty acids have been heretofore used at a high temperature of about 200° C. as the catalysts for the ester interchange reaction (U.S. Pat. No. 2,879,281, Brokaw British Pat. No. 753,880) but it has never been expected that the ester interchange reaction of methyl (metha)acrylate and glycide occurs at low temperatures of lower than 100° C. as in the present invention.

The present invention consists in a method for producing glycidyl (metha)acrylate by using a metal salt of a fatty acid as the catalyst in the ester interchange reaction of methyl (metha)acrylate and glycide.

The catalysts to be used in the present invention are metal salts of fatty acids having 2 to 22 carbon atoms and as the fatty acids, mention may be made of acetic acid, propionic acid, butyric acid, caproic acid, capric acid, caprylic acid, lauric acid, myristic acid, palmitic acid, stearic acid, hydroxystearic acid, arachic acid, behenic acid, acrylic acid, methacrylic acid, oleic acid, linolic acid, etc., and as the mixture of the above described fatty acids, mention may be made of beef tallow fatty acid.

As the metal salts, mention may be made of potassium, sodium, magnesium, calcium, barium, zinc, lead, tin, copper and nickel salts and the like. Among them, calcium stearate, calcium hydroxystearate, calcium salt of beef tallow fatty acid and potassium methacrylate are particularly effective as the catalyst.

An amount of the catalyst used is 0.005 to 0.1 mol per 1 mol of glycide, more preferably 0.01 to 0.05 mol.

In the present invention, as the starting materials, methyl methacrylate or methyl acrylate and glycide are used.

The reaction is carried out in the presence of the known polymerization inhibitors, for example, hydroquinone, hydroquinone monomethyl ether, aminophenol, diphenylamine, phenothiazine and the like and the addition amount is preferred to be 50 to 1,500 ppm based on the total weight of the starting materials.

Methyl (metha)acrylate and glycide are reacted at a molar ratio of 15:1 to 2:1, preferably 10:1 to 4:1. The reaction is carried out at a temperature of 40° to 100° C., preferably 50° to 80° C.

The reaction is carried out under a reduced pressure while introducing a small amount of air into the reaction mixture and methanol simultaneously by-produced in continuously removed as an azeotropic mixture with an excess amount of methyl (metha)acrylate so as to maintain always the molar ratio of the reaction system at 15:1 to 2:1. If the reaction is carried out in such a manner, the reaction is completed in 1.5 to 4 hours. Then, the reaction mixture is cooled and the catalyst is removed and recovered by filtration, after which the filtrate is continuously distilled to obtain glycidyl (metha)acrylate.

Any of the catalysts to be used in the present invention do not cause polymerization nor produce by-product. Accordingly, the resulting glycidyl (metha)acrylate has a high purity (more than 98%) and is obtained in a high yield (89 to 93%).

Any of the catalysts to be used in the present invention can be completely removed and recovered easily by simple filtration from the reaction mixture. Therefore, the filtrate can be immediately and continuously distilled and glycidyl (metha)acrylate can be very advantageously obtained.

Furthermore, the catalyst to be used in the present invention is a metal salt of a fatty acid, so that the catalyst is safe and has the merit that particular caution is not needed in the handling and storage.

The following examples are given for the purpose of illustration of this invention and are not intended as limitations thereof.

EXAMPLE 1

To 3 l of flask equipped with a thermometer, an air feed tube, a dropping bottle and a distillation column were charged 1,000 g (10 mol) of methyl methacrylate, 148 g (2 mol) of glycide and 0.4 g of hydroquinone monomethyl ether as a polymerization inhibitor. Then 16.4 g (0.027 mol) of calcium stearate was added thereto as the catalyst. The resulting mixture was heated at a temperature of 70° to 80° C. under a reduced pressure of 180 to 250 mmHg while introducing a slight amount of air to immediately and continuously distill off the formed methanol as an azeotropic mixture with methyl methacrylate. Caution was paid so than the molar ratio (methyl methacrylate:glycide) of the reaction system does not become less than 4:1 during the reaction and an amount of the distilled liquid and the composition ratio were measured and when the molar ratio lowered to the value lower than the defined ratio, a give amount of methyl methacrylate was added from the dropping bottle. The reaction was completed in 100 minutes. It was confirmed by gas chromatography that the conversion of glycide was 99.4% and the formation of glycidyl methacrylate was 98.7%.

After the reaction was completed, the reaction mixture was immediately cooled and the catalyst was recovered by filtration and the filtrate was subjected to a continuously distilling column to recover an excess amount of methyl methacrylate (boiling point: 100.8° C./760 mmHg) and then 262 g of glycidyl methacrylate (boiling point: 75° C./10 mmHg) was obtained by the continuous distillation (purity: 99.2%, yield: 92.1%).

EXAMPLE 2

The reaction was made in the same manner as described in Example 1 by adding 4,500 g (45 mol) of methyl methacrylate, 370 g (5 mol) of glycide, 1 g of diphenylamine as the polymerization inhibitor and 32 g (0.05 mol) of calcium hydroxystearate as the catalyst. The formation of glycidyl methacrylate was 97.5%. Then the distillation was effected in the same manner as described in Example 1 to obtain 645.6 g of glycidyl methacrylate (purity: 98.5%, yield: 90.8%).

EXAMPLE 3

The reaction was made in the same manner as described in Example 1 by adding 2,500 g (25 mol) of methyl methacrylate, 370 g (5 mol) of glycide, 1 g of phenothiazine as the polymerization inhibitor and 15.6 g (0.05 mol) of potassium salt of beef tallow fatty acid as the catalyst. The formation of glycidyl methacrylate was 97.0%. 638.5 g of glycidyl methacrylate was obtained by the distillation (purity: 98.0%, yield: 89.8%).

EXAMPLE 4

The reaction was made in the same manner as described in Example 1 by adding 2,500 g (25 mol) of methyl methacrylate, 370 g (5 mol) of glycide, 1 g of phenothiazine as the polymerization inhibitor and 6.21 g (0.05 mol) of potassium methacrylate as the catlayst. The formation of glycidyl methacrylate was 97.0%. 633 g of glycidyl methacrylate was obtained by the distillation (purity: 98.0%, yield: 89%).

EXAMPLE 5

To the same apparatus as described in Example 1 were added 2,150 g (25 mol) of methyl acrylate, 370 g (5 mol) of glycide, 1 g of phenothiazine as the polymerization inhibitor and 41.3 g (0.068 mol) of calcium stearate as the catalyst. The resulting mixture was heated at a temperature of 50° to 70° C. under a reduced pressure of 200 to 400 mmHg while introducing a slight amount of air to effect the reaction while distilling off the formed methanol as an azeotropic mixture with methyl acrylate. The reaction was completed in 2 hours. The formation of glycidyl acrylate was 96.5%. 575 g of glycidyl acrylate was obtained by the distillation (purity: 98.1%, yield: 89.7%).

What is claimed is:

1. A method for producing glycidyl methacrylate or glycidyl acrylate, which comprises using a metal salt, selected from the group consisting of potassium, sodium, and calcium salts, of a fatty acid having from 2 to 22 carbon atoms, as a catalyst in an ester interchange reaction of methyl methacrylate or methyl acrylate and glycide, wherein the molar ratio of methyl methacrylate or methyl acrylate to glycide is 15:1 to 2:1, the reaction being carried out at a temperature of 40°–100° C. under reduced pressure while introducing a small amount of air into the reaction mixture, by-product methanol being continuously removed as an azeotropic mixture with an excess amount of methyl methacrylate or methyl acrylate.

2. The method as claimed in claim 1, wherein the catalyst is calcium stearate, calcium hydroxystearate, potassium salt of beef tallow fatty acid or potassium methacrylate.

3. The method as claimed in claim 1, wherein an amount of the catalyst is 0.005 to 0.1 mol per 1 mol of glycide.

4. The method as claimed in claim 1, wherein the reaction is carried out in the presence of a polymerization inhibitor of hydroquinone, hydroquinone monomethyl ether, aminophenol, diphenylamine or phenothiazine.

5. The method as claimed in claim 4, wherein an amount of the polymerization inhibitor is 50 to 1,500 ppm based on the total weight of the starting materials.

6. A method as claimed in claim 1, wherein the molar ratio of methyl methacrylate or methyl acrylate to glycide is 10:1 to 4:1.

* * * * *